US006375962B2

(12) United States Patent
Jenner et al.

(10) Patent No.: US 6,375,962 B2

(45) Date of Patent: *Apr. 23, 2002

(54) BARRIER CREAM COMPRISING HEXAMETHYLENETETRAMINE OR DERIVATIVE THEREOF

(75) Inventors: John Jenner; Colin N Smith; Robert P Chilcott; Christopher D Lindsay, all of Salisbury (GB)

(73) Assignee: The Secretary of State for Defence in Her Britannic Majesty's Government of the United Kingdom of Great Britain and Northern Ireland, Hampshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/767,136

(22) Filed: Jan. 23, 2001

Related U.S. Application Data

(62) Division of application No. 09/180,749, filed as application No. PCT/GB97/01348 on May 16, 1997, now Pat. No. 6,224,885.

(30) Foreign Application Priority Data

May 17, 1996 (GB) ............................................ 9610405
Jun. 13, 1996 (GB) ............................................ 9612417

(51) Int. Cl.[7] .......................... A61K 7/00; A61K 31/02; C07D 487/12

(52) U.S. Cl. ....................... 424/401; 424/400; 424/405; 424/406; 424/78.05; 544/185; 514/723; 514/759; 514/946; 514/947

(58) Field of Search ................................ 424/400, 401, 424/405, 406, 78.05; 514/723, 759, 947, 946; 544/185

(56) References Cited

U.S. PATENT DOCUMENTS

| | | | | |
|---|---|---|---|---|
| 3,154,546 A | * | 10/1964 | Chessin et al. | 260/248.5 |
| 4,456,722 A | * | 6/1984 | Foley | 524/413 |
| 5,607,979 A | * | 3/1997 | McCreery | 514/759 |

FOREIGN PATENT DOCUMENTS

| | | | |
|---|---|---|---|
| EP | 0 226 337 | | 6/1987 |
| GB | 1 101 830 | | 1/1968 |
| GB | 1525971 | * | 9/1978 |
| JP | 49 012 040 | | 2/1974 |
| JP | 49012040 | * | 2/1974 |
| RU | 2 007 164 | | 2/1994 |
| RU | 2 036 636 | | 6/1995 |
| RU | 2036636 | * | 6/1995 |

OTHER PUBLICATIONS

J. Chem. Soc. Perkin Transactions 2, vol. 11, 1994, Letchworth GB, pp. 2325–2328, Bellamy: "Reaction of Gaseous Sulfur Mustard with Zeolite 13X".

* cited by examiner

*Primary Examiner*—Thurman K. Page
*Assistant Examiner*—Lakshmi Channavajjala
(74) *Attorney, Agent, or Firm*—Nixon & Vanderhye

(57) ABSTRACT

Skin protection agents such as topical compositions which can prevent the passage of toxic chemicals through the skin, such as barrier creams. Formulations may contain hexamethylene tetramine or derivatives or analogues thereof, which react with alkylating agents such as sulfur mustard, and which are suitable for formulation into topical compositions. The formulations additionally may contain perfluorinated polymeric compounds which are effective barrier compounds for a range of toxic chemicals.

7 Claims, 6 Drawing Sheets

BARRIER CREAM COMPRISING HEXAMETHYLENETETRAMINE OR DERIVATIVE THEREOF

This is a division of application Ser. No. 09/180,749, filed Dec. 7, 1998, now U.S. Pat No. 6,224,885, which is a 371 of PCT/GB97/01348 filed May 16, 1997 the entire content of which is hereby incorporated by reference in this application.

The present invention relates to skin protection agents, in particular to topical compositions which can prevent the passage of toxic chemicals through the skin, such as barrier creams.

There are many occasions where people are exposed to chemicals or agents which have some degree of toxicity and which may penetrate the skin. It is often desirable or necessary to prevent contact of these chemicals to the skin as far as possible.

For instance, many volatile pesticides can provide a potential hazard to operators applying them. Examples of such pesticides include volatile insecticides, particularly organophorphorus insecticides such as isofenphos, or diethyl toluimide. In other industrial applications, workers exposed to industrial solvents such as acetone, chloroform, methanol, hexane, benzene and toluene, may require protection.

In chemical warfare situations, highly toxic volatile chemicals, which may penetrate the skin can be used. These include Sarin, Soman and Tabun as well as sulphur mustard and Lewisite.

Sulphur mustard (SM) is a vesicating chemical used as a war gas. It is a potent alkylating agent which is thought to be toxic to living tissue by virtue of its ability to alkylate vital cellular constituents (Fox M. and Scott M., Mut. Res (1980) 75, 131–168). SM has been shown to alkylate DNA. RNA and proteins (Paprimeister B. et al., (1991) Medical Defence against Mustard Gas (CRC Press) 91–122), though a causal link between alkylation of either of these cellular constituents and vesication has yet to be established.

Although considerable protection from toxic chemical vapours can be afforded by protective clothing in the form of respirators, charcoal cloth garments and gloves these measures may not be completely effective in all circumstances. The use of a barrier cream might augment the charcoal cloths used in protective clothing and permit tasks requiring manual dexterity to be carried out in an atmosphere containing chemical agent vapour, without gloves for short periods.

Traditional barrier creams have placed a passive barrier between the skin and the environment which prevent access of chemicals generally to the surface of the skin. Cream bases consist of an emulsion, either oil in water or water in oil (Barry B. W (1983) Drugs Pharmaceutical Sci 18 296–350). Water in oil emulsions are unsuitable as barrier creams because the oily deposit they leave on the surface of the skin results in loss of tactility. On their own oil in water type creams have required layers of greater than 0.56 mm to be established and maintained on the skin in order to be effective. More recently creams based on silicone derivatives have allowed effective barriers against general chemical penetration of the skin to be produced using very thin layers of cream (EP-A-0401840, Japanese Patent Appln no. 57-26610).

Formulation of a reactive chemical which reacts with specific target chemical groups in the cream converts a passive barrier cream into an active cream which sequesters and inactivates a specific group of toxic chemicals before they can reach the living layers of the skin.

The use of reactive molecules which would inactivate SM before it could react with cell constituents has been investigated. A series of sulphydryl compounds designed to enter the living cell and fortify it against reactive compounds such as SM has already been disclosed in PCT GB91/01462 and GB90148994.5.

It is known that increased levels of GSH and GSH synthetic enzymes (Evans et al., Cancer Res. 47 2525–2530, Ahmed S. et al., J. Biol. Chem. 262 15048–15053, and Ahmed S. et al., J. Cellular Physiol. 131, 240–246) confer resistance to nitrogen mustard on cell cultures. In previous studies attempting to protect cell cultures against SM, Gross C. L. and Smith N. J. (Proc. 1993 Med. Def. Bioscience Rev. (US Army Medical Research and Development Command) 1 141–147) found that human lymphocytes pretreated with 10 mM L-oxothiazolidine-4-carboxylate for 48 hours and subsequently exposed to 10 $\mu$M SM were 20% more viable than SM only treated cells 48 hours after exposure. Other attempts to protect human lymphocyte cultures (Gross et al. Cell Biology and Toxicology (1993) 9 259–268) by raising intracellular levels of GSH using N-acetyl cysteine (10 mM) and subsequently challenging with 10 $\mu$M SM increased viability by only 15 to 19% of control cultures at 48 hours.

The stratum corneum is the dead layer of skin which acts as a barrier to chemical penetration through the skin (Tregear R. T. (1966) Theoretical Exp. Biol. 5, 21–22). The stratum corneum is composed of the dead "protein ghosts" of the living cells of the epidermal layer of the skin, surrounded by a unique mixture of lipids which the cells of the epidermis produce (Wertz P. W. et al., (1989) "Stratum corneum: Biological and Biochemical considerations" in Transdermal Drug Delivery, Ed Hadgraft J & Guy R A. 1–22).

HMT has been used prophylactically to protect rabbits and man against exposure to lethal phosgene doses (Diller W. F. J. Occ. Med (1978) 20 189–193).

The present application relates to a topical composition for use particularly against SM. In particular the invention relates to an active barrier cream for SM.

The present invention provides a composition which comprises a composition for topical application which comprises hexamethylene triamine or analogues or derivatives thereof.

HMT has the following structure (I)

(I)

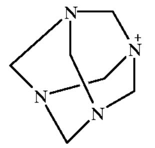

It is believed that because the structure of HMT contains four nucleophilic nitrogen groups, with a similar electronic structure to N-7 in guanine, it neutralises the bifunctional SM more effectively than conventional monofunctional thiol ligands.

Suitable analogues of HMT are compounds which have organic moieties conjugated to the HMT cage structure for example of formula (II)

(II)

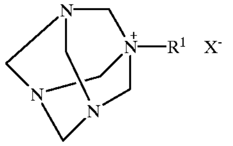

where $R^1$ is an organic group and X is a anion.

The HMT moiety will hereinafter be represented as #.

Examples of suitable groups for $R^1$ include optionally substitited straight or branched hydrocarbon chains such as alkyl chains, having from 1 to 50 carbon atoms, for example from 6 to 32 carbon atoms. In particular, the hydrocarbon chains are optionally substituted by one or more substituents selected from aryl, such as phenyl, optionally substituted by halogen, and/or halogen atoms, such as fluorine, chlorine or bromine and particularly fluorine. A particular group $R^1$ is a fluorobenzyl or a group $(CH_2)_nCH_3$ where n is from 8 to 20, suitably about 17.

Further examples of such compounds include compounds of the following formulae:

$$(\#)\text{—}CH_2(CH_2)_{22}CH_3$$

$$(\#)\text{—}CH_2(CH_2)_{14}CH_3$$

where # represents a hexamethyltetraminyl group.

Suitable anions X are chosen such that the compound of formula (II) are pharmaceutically acceptable salts, in particular those which are suitable for topical application, for example halide ions such as iodides or bromides.

Suitable derivatives of HMT are made by the conjugation of HMT with either the normal constituents of barrier creams (such as palmitic or stearic acids), the normal constituents of the stratum corneum (cholesterols or ceramides) or large long chain aliphatic molecules. Suitably the long chain aliphatic molecules have from 16 to 32 carbon atoms. Particular aliphatic molecules which may be employed are fatty acids having from 16 to 32 carbon atoms.

Analogues of formula (II) are suitably prepared by reacting HMT with a compound of formula (III)

$$Y\text{—}R^1 \qquad \text{(III)}$$

or a salt thereof; where $R^1$ is as defined in relation to formula (II) and Y is a leaving group, and thereafter if necessary converting a salt produced to a different salt.

Suitable leaving groups for Y include halogen such as fluorine, chlorine or bromine, particularly bromine, as well as mesylate and tosylate. The reaction is suitably effected in an organic solvent, for example chloroform, alcohols such as methanol or ethanol, acetonitrile at elevated temperatures conveniently at the reflux temperature of the solvent.

Salts of formula (III) may be any salt as convenient depending upon the particular nature of the reagents involved. They may subsequently be changed to a different pharmaceutically acceptable salt using ion exchange procedures, for example by passing the compound down an ion exchange column as is conventional in the art.

Suitably the composition further comprises a cream base.

These compositions place an active barrier between the cellular constituents of the skin and the outside world, at the level of the dead layer of the skin, the stratum corneum. This is achieved by a molecule which reacts with and sequesters SM which is suitably fixed on the surface of the strateum corneum in a very thin layer using a barrier cream base.

Suitably the composition contains further active reagents, in particular other nucleophilic scavengers. Such groups are useful because SM reacts readily with a wide range of nucleophilic groups found in biological systems. The most important of these are thought to be the N-7 groups of guanine residues in nucleic acids and the sulphydryl groups of cysteine containing peptides and proteins, the affinity of SM for the former biological ligand in particular, dictates the necessity of having protective measures in place prior to SM exposure. Since SM is bifunctional it can crosslink biomolecules, forming DNA crosslinks between guanine residues (Papirmeister B et al., Medical Defence against Mustard Gas (CRC Press Inc. Bocca) (1991) pp106).

A preferred group of further reagents for use in the composition of the invention include compounds which have nucleophilic nitrogen and/or sulphur atoms, preferably nitrogen.

Examples of sulphur containing nucleophilic compounds include glutathione (GSH) and esters of cysteine, for example as shown in WO 92/04024.

When two different species of nucleophile (ie N and S) are used as extracellular scavengers of SM, they unexpectedly have had an increased protective effect in this study, compared to using the compounds singly. Thus a composition which comprises both nucleophilic nitrogen and sulphur are preferred. Such compositions include combinations of HMT or derivatives or anlogues and GSH. Alternatively, thiolated forms of the conjugating agents mentioned above, such as thiol derivatives of cholesterol or a ceramide may be used.

In addition, it has been shown that the use of ligand mixtures increases the capacity of protection media to reduce SM-induced cytotoxicity without synergistic cytotoxic effects.

Small molecules in a barrier cream can diffuse through the skin and be absorbed into the blood which may result in local irritation or systemic toxicity. Therefore, in a preferred embodiment, the cream includes large lipophilic molecules which do not penetrate the skin leaving the reactive molecule either on the surface of the skin or retained within the superficial layers until they slough off in the normal cycle of the epidermal tissue.

Consequently in a preferred embodiment, the active barrier cream of the invention is prepared by forming a complex comprising a suitable reactive molecule and a large lipophilic molecule and the resultant complex is formulated into a barrier cream base.

A specific embodiment of the invention is a reactive barrier cream which comprises HMT in an oil in water emulsion cream base.

However, it has been found that a particularly advantageous carrier for the compositions comprises a perfluorinated polymeric compound.

Such compounds have a low surface energy and thereby prevent partitioning of the volatile chemical into the topical composition and skin. Indeed it has been found that such compounds can act as effective barrier creams when used alone and this forms a further aspect of the invention.

Suitably the perfluorinated polymeric compound is of formula (IV):

$$CF_3O\text{—}[CF(CF_3)CF_2O]_n\text{—}[CF_2O]_m\text{—}CF_3 \qquad \text{(IV)}$$

where n and m are independently selected from 4 to 150, suitably from 6 to 140.

Suitably the compound of formula (IV) is in the form of an oil. Examples of such compounds are set out in the following Table:

| Compound No. | n | m |
|---|---|---|
| 1 | 140 | 13 |
| 2 | 40 | 11 |
| 3 | 25 | 6 |
| 4 | 18 | 8 |
| 5 | 6 | 6 |
| 6 | 25 | 9 |
| 7 | 14 | 6 |
| 6 | 16 | 6 |

These compounds are available commercially from Aldrich Chemical Company, Gillingham, Dorset and are sold under the trade name "Fomblin"™. Other compounds of formula (IV) may be prepared using conventional methods.

The perfluorinated compounds produce a significantly improved barrier to SM than conventional oil-in-water emulsions, which under some conditions, may actually trap the SM and increase the penetration rate.

The compositions of the invention comprise a substantial portion of perfluorinated polymeric compound for instance up to 100% w/w perfluorinated compound. Suitably, the compositions comprise from 30–100% w/w perfluorinated compound and preferably in excess of 50% w/w. Where 100% prefluorinated compound is used, this must comprise an oil.

These compositions may further comprise active agents other than or in addition to HMT or analogues or derivatives thereof as described above, which react with or sequester the chemical which it is intended should be prevented from reaching the skin.

For instance, reactive molecules which would inactivate for example, SM before it could react with cell constituents may be included. Such compounds include compounds disclosed in PCT GB91/01462 and GB90148994.5 or WO 92/04024 as mentioned above. A particular reactive agent which may be used in the formulations of the invention is potassium butadione monoximate.

Where present, preferred ratios of the active compound: perfluorinated compound in a barrier cream formulation are, as before, from 5:95 to 60:40 w/w for instance from 10:90 to 60:40 w/w, most preferably 25:75 w/w.

The compositions may be in the form of oil in water or water in oil emulsions. Other components of such emulsions include emulsifying agents and oils conventionally used in barrier cream type formulations such as mineral or silicone oils. However, the compositions are preferably oils rather than emulsions.

Preferably, the compositions of the invention further contain lower molecular weight perfluorinated compounds such as polytetrafluoroethylene. These compounds can affect the viscosity of the formulation, making them more effective barriers. Suitable compounds of this type are available from ICI plc. They have a molecular weight of the order of $10^6$, and a particle size of approximately 6microns.

The present inventors have studied the ability of HMT to protect cells against the toxic effects of SM in culture and to prevent the penetration of SM through isolated skin, to assess the feasibility of its prophylactic use to prevent SM induced skin injury. Penetration of radiolabelled SM across human stratum corneum has been measured in vitro using glass diffusion cells.

In the cell culture study, Simian virus keratinocyte-14 (SVK-14—a human keratinocyte line transformed with the SV40 virus) cell cultures were used to assess the protection afforded by a prophylactic mixture of sulphur and nitrogen containing compounds against SM, and the effect of using the compounds singly. Mitotically active cells are known to be more sensitive to the effects of DNA alkylating agents such as SM (Fox M. & Scott M. et al., Mut. Res. 75 131–168), since the formation of cross-linked DNA lesions prevents mitosis, leading to unbalanced metabolism and cell death (Cohen et al., Proc. NY Nat. Acad. Sci. 40 885–893).

The use of an actively mitosing, keratinocyte-derived cell line as used in the present study has several important advantages over resting peripheral blood lymphocytes used in the studies of Gross et al. (supra): firstly, the epithelial morphology of the SVK culture means that it is a better model of the main targets of SM intoxication, namely the basal epidermis, the broncho-epithelium and the corneal epithelium; secondly, SVKs are an attached cell-line, enabling the study of specific intercellular interactions following SM exposure; finally, because the SVK cultures are mitotically active they will be more susceptible to SM for the reasons outlined above.

Altogether, the use of SVK cultures represents a more severe test of the efficacy of putative prophylactic regimes than does the use of peripheral blood lymphocytes. Consequently, the level of protection of the SVK cultures observed in this study is far greater than that achieved in previous studies aimed at increasing intracellular GSH levels.

In the present tests, assessment of the pretreated cultures 96 hours after exposure to SM demonstrated a significant increase in the viability of the SVK cells compared to those exposed to SM. Culture viability was measured using the NR assay. This involves the uptake of NR dye into intracellular vesicles such as lysosomes and gives a measure of cellular activity as well as membrane integrity.

63.3% of cells in cultures pretreated with 4 mM GSH/10 mM HMT remained viable compared to 33.5% of SM exposed cells, this was mirrored in the photomicrographs (not included) showing SM exposed and pretreated cultures respectively. SM exposed cells have taken up the dye but the drastically altered cellular morphology (extended cytoplasm and congregation of lysosomes around the swollen nucleus) indicates that these cells are not in a truly viable and proliferative state. In comparison, the pretreated cultures show protection of the cells with a preserved monolayer, a great reduction in the number of hyperplasmic cells and a more diffuse distribution of the lysosomes in the cytoplasm.

Cell numbers were measured using crystal violet staining of DNA. Pretreatment of the SVK cultures with 4 mM GSH/10 mM HMT did not significantly alter the growth rate compared to the control, however the difference between pretreated cultures compared to those exposed to SM is marked. Not only is there a preservation of cell numbers at every time-point but also the rate of culture depopulation is less and there is an eventual recovery of the population by 96 hours at a comparable growth rate to the control. The use of either 8 mM GSH or 10 mM HMT singly was not as effective as using the compounds in combination at the 72 hour time-point, with increases in viability of 19.8% or 22.6% compared to 29.8%. The use of 16 mM GSH gave an increase in viability of 20.6% at 72 hours compared to the SM control ($p<0.001$), whilst the use of 20 mM HMT did not alter the toxicity of SM ($p>0.05$) at 72 hours. The use of GSH and HMT in combination confered greater protection on the cultures than higher concentrations of the single prophylactics.

Penetration of radiolabelled SM across rubber latex membranes and human epidermal skin membranes has been measured in vitro using glass diffusion cells is also reported hereinafter.

In a diffusion cell system the chemical diffuses through the membrane (the penetrant) by partitioning between its vehicle and the membrane, then between the membrane and the receptor fluid. When the thermodynamic activity, of the penetrant (usually synonymous with concentration) on both sides of the membrane is equal the system is in equilibrium and there will be no further change in the amount of penetrant in the receptor fluid.

In certain diffusion studies reported hereinafter, the ability of each composition to slow the rate of penetration through the membrane was shown by a calculation of the retardant index (RI) using the equation $$RI=J_{max}(\text{control})/J_{max}(\text{treated})$$

where $J_{max}$ is the maximum penetration rate of sulphur mustard through control (untreated) and treated membranes.

When a compound reacts with the penetrant on the surface of the membrane and forms a product which does not penetrate the membrane, the total amount of penetrant in the receptor fluid at equilibrium will be reduced. In such a case, and if the penetrant is applied as an undiluted liquid the measured maximum rate of penetration would only be reduced if the presence of the product reduces the thermodynamic activity of the penetrant.

When using radiolabel to measure the amount of penetrant in the receptor chamber no distinction can be made between unreacted penetrant and product. Therefore if the product also penetrates the membrane the measured maximum diffusion rate and total amount penetrating will be increased.

When the reactive protectant is applied to the membrane in a cream base the penetrant must partition into the cream and then into the membrane in order to enter the receptor chamber. The partitioning of the penetrant into the cream can thus modify the rate of penetration by altering the partitioning of the penetrant into the membrane. The reactive protectant must also retain its reactivity with the penetrant within the chemical environment of the cream base.

In diffusion studies reported hereinafter, the reduction in the total amount of SM penetrating the epidermal membranes pretreated with HMT alone, without effect on the maximum flux rate, supports the hypothesis that HMT is reacting with SM to form a product which does not cross the membrane.

Mixing HMT with oil in water cream bases retains the reduction in total amount penetrated indicating that any reaction also occurs in this medium. The reduction in maximum flux rate observed in a cream base, such as Stokoderm® obtainable from Arco Skin Care Products, Hull, may result from a reduction in partitioning of SM into the epidermal membranes from the cream. The possibility that the product of any reaction may partition into the membrane from the cream base cannot be discounted and may explain the slight increase in maximum penetration rate measured through the oil in water emulsions containing beeswax and brij 52.

In summary, the reduction in the cytotoxicity of SM and its penetration of epidermal membranes in the presence of HMT support the use of HMT or one of its analogues as a reactive constituent of barrier creams.

As illustrated hereinafter, formulations referred to in this application can reduce the rate of penetration of SM through isolated stratum corneum by five fold, and sometimes up to 45 fold, and reduce the total amount penetrated by up to 90%.

BRIEF DESCRIPTION OF THE DRAWINGS

The following Examples illustrate the invention. In these examples reference is made to the attached Figures in which.

EXAMPLE 1

Cell Culture Experiments

A human keratinocyte culture, specifically SVK-14 human keratinocyte cells were used in these experiments.

Tissue culture plastics were obtained from J. Bibby Science Products Ltd, Stone, Staffs. The SVK cells were grown in a medium comprising 84% v/v Dulbecco's modified Eagle's medium (DMEM), 16% v/v foetal calf serum (FCS), containing 100 IU/ml penicillin, 100 $\mu$g/ml streptomycin and 2 mM glutamine (referred to hereinafter as SVK medium). The cultures were maintained in a 37° C. incubator in a humidified atmosphere of 95:5 air:carbon dioxide. The cells were grown to confluency in 150 $cm^2$ flasks, removed from the flasks by incubation at 37° C. with a trypsin/EDTA solution (Sigma), for 5–10 minutes, sown in 96 well cell culture plates (40,000 to 60,000 cells per well) and allowed to attach for 24 hours.

Solutions of GSH (8 mM and 16 mM) and HMT (10 mM and 20 mM) in DMEM, containing 100 IU/ml penicillin, 100 $\mu$g/ml streptomycin and 2 mM glutamine, were mixed to give four solutions herein after referred to as protection media:

1 4 mM GSH, 5 mM HMT;

2 4 mM GSH, 10 mM HMT;

3 8 mM GSH, 5 mM HMT;

4 8 mM GSH, 10 mM HMT,

Protection media and single solutions of 8 mM GSH and 10 mM HMT, prepared as above, were sterile filtered before use.

Figure 1:
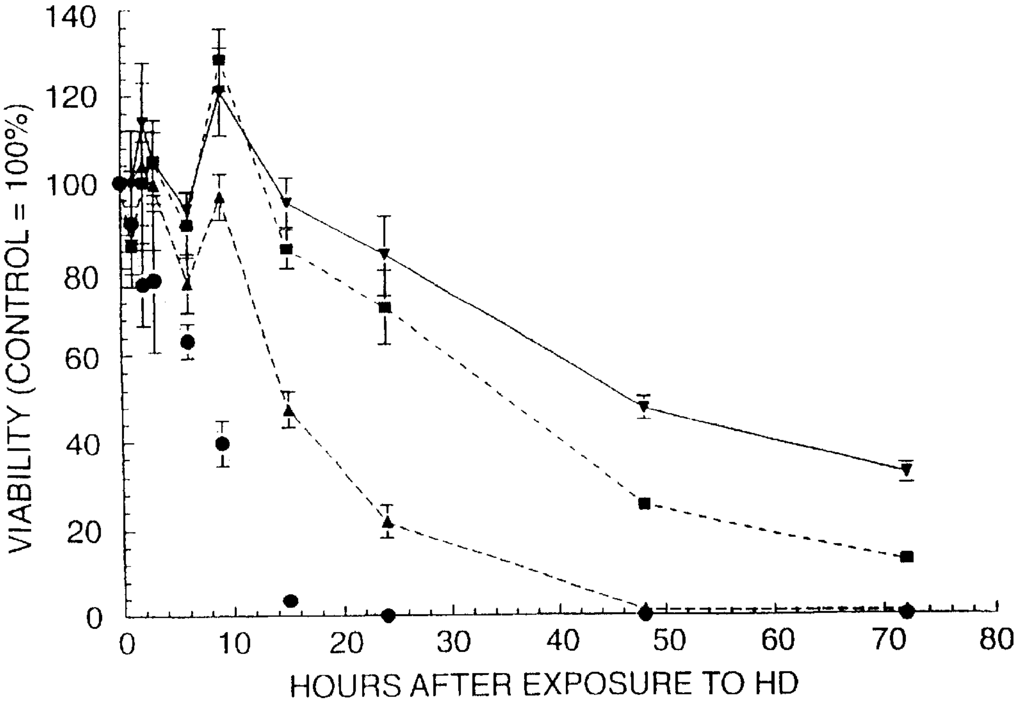
FIG. 1 is a graph showing the effect of 2 (▼), 10 (■), 50 (▲) and 250 μM SM (●) on the viability (Neutral Red assay) of SVK-14 cultures with time. Data are shown as the mean±S.E.M. (n=8) expressed as a percentage of the untreated control.

The response of the SVK-14 cell line to sulphur mustard exposure was first assessed by comparing dose response curves for four concentrations of SM (2, 10, 50 and 250 $\mu$M) at time points up to 72 hours (FIG. 1). Cell viability was assayed using neutral red (NR) dye retention (Griffiths et al, Toxicology (1994) 90 11–27) at various time points following SM exposure. Results are expressed as a percentage of live control (non-SM exposed) cultures.

The deleterious effects of SM on cell viability were found to be both time and concentration dependant and the time taken to reach the $LC_{50}$ (Lethal concentration 50—the concentration which reduces cell culture viability to 50% of control levels) was inversely proportional to the concentration of SM used (2, 10, 50 and 250 $\mu$M SM took 47, 35, 15 and 8 hours respectively). Subsequently 10 $\mu$M SM was used as a standard dose against which the efficacy of the pretreatment could be assessed.

Ninety six well culture plates were pretreated by replacing the culture medium for 100 $\mu$l of one of the protection media or 100 $\mu$L DMEM containing, 100 IU /ml penicillin, 100 $\mu$g/ml streptomycin and 2 mM glutamine, as non-pretreated controls. The cultures were then incubated in the presence of these solutions for 37° C. in a humidified atmosphere of 95:5 air:carbon dioxide. After 1 hour 100 $\mu$l SM solution in Hank's buffered salt solution (HBSS) (10 $\mu$M, prepared by dilution of a 50 mM stock solution in isopropanol) was added to each well and the plates incubated for a further 1 hour at 37° C. in the same atmosphere. The solutions were removed from the wells and 100 $\mu$l of SVK medium was added. The cultures were incubated at 37° C. in the atmosphere described above for periods of up to 96 hours. At selected time points, viability was determined by the NR and crystal violet assay.

It was found that the addition of SM (10 $\mu$M) to the SVK cultures resulted in a steady decline in viability over time so that at 24, 48, 72 and 96 hours viability (as determined by the NR assay, FIG. 2) had fallen to 85.7, 54, 40.8 and 33.5% of the control cultures. This contrasts with cultures to which SM was applied in the presence of 4 mM GSH/10 mM HMT, for viability was then maintained at 99, 69.7, 58.3 and 63.3% respectively at the above time points. The viability of the pretreated cultures was therefore 1.9-fold (or 89%) greater than non-protected cultures 96 hours after SM exposure. This difference was significantly different ($p<0.001$) when measured by ANOVA with Tukey post test.

Cell number was determined by nuclear staining with 0.1% (w/v) crystal violet after the method of Gillies et al, (Analytical Biochem. (1986) 159 109–113). Results were expressed as the optical density measured at 620 nm.

Figure 3:
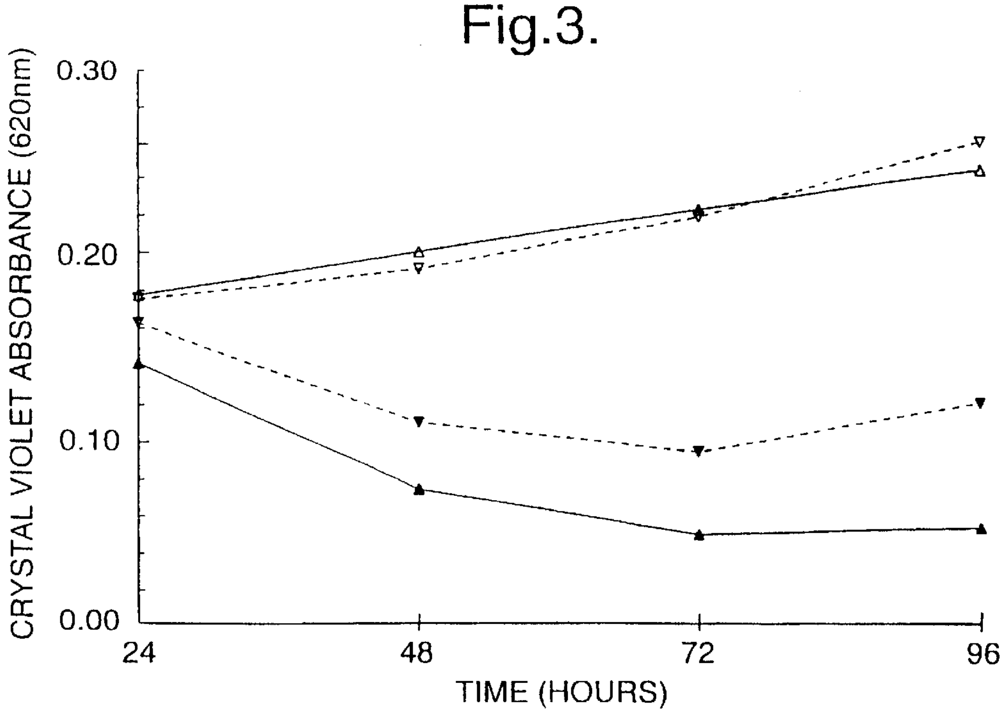
FIG. 3 shows the effect on cell numbers of pretreatment of SVK-14 cultures with a mixture of 4 mM GSH/10 mM HMT prior to exposure to 10 μM SM. Cell numbers of untreated control cultures (Δ), pretreated control cultures (▽), pretreated cultures exposed to SM (▼) and untreated cultures exposed to SM (▲) was measured using the crystal violet assay. Data are shown as the mean±S.E.M. (n=15)

The results are shown in FIG. 3 and are broadly similar, although at 96 hours the number of cells in the pretreated cultures was 2.3-fold (or 131%) greater than in the unprotected cultures. This difference was also significantly different ($p<0.001$) when measured by ANOVA with Tukey post test.

The other protection media comprising different combinations of GSH/HMT protectants conferred similar levels of protection on SVK cell cultures exposed to SM when measured by NR assay (Table 1) and crystal violet assay (Table 2).

TABLE 1

| | Relative viability of pretreated cultures compared to cultures only exposed to 10 $\mu$M SM | | | |
|---|---|---|---|---|
| {Private} Drug Combination | 24 h | 48 h | 72 h | 96 h |
| 10 $\mu$M SM | 93.8 ± 0.56 | 59.1 ± 0.48 | 40.0 ± 0.57 | 28.7 ± 0.28 |
| 4 mM GSH/5 mM HMT + 10 $\mu$M SM | 100.3 ± 0.56* | 74.3 ± 0.48* | 50.9 ± 0.85* | 55.1 ± 0.55* |
| 10 $\mu$M SM | 85.7 ± 1.4 | 54.0 ± 0.52 | 40.8 ± 0.83 | 33.5 ± 0.27 |
| 4 mM GSH/10 mM HMT + 10 $\mu$M SM | 99.0 ± 1.4* | 69.7 ± 1.82* | 58.3 ± 0.56* | 63.3 ± 0.53* |
| 10 $\mu$M SM | 93.4 ± 0.57 | 63.2 ± 0.75 | 38.2 ± 0.9 | 31.0 ± 0.54 |
| 8 mM GSH/5 mM HMT + 10 $\mu$M SM | 101.1 ± 0.85* | 80.7 ± 0.5* | 63.9 ± 0.3* | 64.2 ± 0.54* |
| 10 $\mu$M SM | 101.9 ± 2.3 | 70.2 ± 0.72 | 35.3 ± 0.91 | 26.9 ± 0.55 |
| 8 mM GSH/10 mM HMT + 10 $\mu$M SM | 116.4 ± 2.3* | 84.9 ± 0.96* | 65.0 ± 0.96* | 62.4 ± 1.1* |

Mean data are shown with standard error of the mean for groups of 15 cultures (as a percentage of the control mean).
*shows significant difference ($p < 0.001$) when measured by ANOVA with Tukey post test.

TABLE 2

| Comparison of cell number between pretreated cultures and those only exposed to 10 mM SM | | | | |
|---|---|---|---|---|
| Drug Combination | 24 h | 48 h | 72 h | 96 h |
| Control | 0.161 ± 0.001 | 0.179 ± 0.001 | 0.218 ± 0.002 | 0.249 ± 0.001 |
| 10 $\mu$M SM | 0.132 ± 0.002 | 0.069 ± 0.001 | 0.056 ± 0.001 | 0.052 ± 0.001 |
| 4 mM GSH/5 mM HMT + 10 $\mu$M SM | 0.134 ± 0.003 | 0.101 ± 0.001* | 0.099 ± 0.001* | 0.103 ± 0.001* |
| Control | 0.178 ± 0.002 | 0.200 ± 0.002 | 0.223 ± 0.002 | 0.244 ± 0.002 |
| 10 $\mu$M SM | 0.141 ± 0.002 | 0.074 ± 0.001 | 0.049 ± 0.001 | 0.052 ± 0.002 |
| 4 mM GSH/10 mM HMT + 10 $\mu$M SM | 0.162 ± 0.002* | 0.110 ± 0.002* | 0.094 ± 0.002* | 0.119 ± 0.001* |
| Control | 0.151 ± 0.002 | 0.162 ± 0.004 | 0.186 ± 0.003 | 0.228 ± 0.002 |
| 10 $\mu$M SM | 0.123 ± 0.001 | 0.057 ± 0.002 | 0.032 ± 0.002 | 0.045 ± 0.001 |
| 8 mM GSH/5 mM HMT + 10 $\mu$M SM | 0.138 ± 0.002* | 0.080 ± 0.002* | 0.085 ± 0.002* | 0.115 ± 0.002* |
| Control | 0.147 ± 0.001 | 0.175 ± 0.002 | 0.202 ± 0.001 | 0.246 ± 0.001 |
| 10 $\mu$M SM | 0.125 ± 0.001 | 0.067 ± 0.001 | 0.047 ± 0.001 | 0.042 ± 0.001 |
| 8 mM GSH/10 mM HMT + 10 $\mu$M SM | 0.136 ± 0.002* | 0.110 ± 0.002* | 0.096 ± 0.002* | 0.104 ± 0.002* |

Data are shown as the mean absorbance (620 nm) with standard error of the mean for groups of 15 cultures.
*shows significant difference ($p < 0.001$) between SM only and treatment + SM when measured by ANOVA with Tukey post test.

Pretreatment with 8 mM GSH only resulted in 111.2, 91 and 60.8% viability when measured by NR assay at 24, 48 and 72 h post exposure respectively (96 h not assayed), compared to the SM-only exposed cells which were 102.9, 68 and 41% viable at the same time points. Pretreatment with 16 mM GSH only resulted in 102.5, 86.8, 76.2 and 80.7% viability when measured by NR assay at 24, 48, 72 and 96 hours post exposure respectively, compared to the SM-only exposed cells which were 97.2, 74.5, 55.6 and 49.1% viable at the same time points. Pretreatment with 10 mM HMT only resulted in 88.9, 83.5 and 59.4% viability when measured by NR assay at 24, 48 and 72 hours post exposure respectively (96 hours not assayed), compared to the SM-only exposed cells which were 91.7, 71.4 and 42.2% viable at the same time points. Pretreatment with 20 mM HMT only resulted in 93.9, 97, 89.2 and 72.2% viability when measured by NR assay at 24, 48, 72 and 96 h post exposure respectively. Treatment with 20 mM HMT and 10 $\mu$M SM resulted in 96.8, 72.3, 41.6 and 12.7% viability when measured by NR assay at 24, 48, 72 and 96 hours post exposure respectively, compared to the SM-only exposed cells which were 99.2, 63.0, 41.8 and 30% viable at the same time points.

When stained with crystal violet, control cultures and those pretreated with protection media demonstrated the epithelial cobblestone morphology and the small cytoplasmic/nuclear ratio normally seen in a confluent monolayer of SVK cells. The application of 10 $\mu$M SM to these cultures resulted in:

1) an enlarged cytoplasmic/nuclear ratio and nuclear swelling
2) plasma membrane blebbing leading to the formation of cell fragments
3) necrotic bodies
4) loss of cell-cell contact and normal epithelial morphology
5) an overall reduction in cell numbers Staining of SM exposed cells with NR showed an accumulation of lysosomes around the nucleus in addition to the above features. The observed changes were time dependant, the longer time points (48–96 hours) showed a progressive destruction of the SVK cultures.

Treatment of SVK cultures with any of the combinations of protection media prior to SM exposure resulted in cultures which after crystal violet staining demonstrated:

1) only limited cytoplasmic swelling
2) preserved epithelial morphology
3) fewer necrotic bodies
4) evidence of mitotic activity In addition, neutral red staining showed a more diffuse distribution of the lysosomes in the cells. These features were observed 96 hours post-exposure.

Treatment of SVK cell cultures with GSH, HMT or combinations of GSH and HMT did not significantly alter the growth of the cells over the course of the experiment when measured by the crystal violet assay, nor alter cellular function when measured by neutral red uptake, indicating that these compounds and combinations were biocompatible.

EXAMPLE 2

Topical Skin Protectant Formulations

Topical skin protectants were formulated using a mixture of barrier cream comprising stearic acid sold under the trade name Stokoderm®, protective compound and optionally with polytetrafluoroethylene, (PTFE). The composition of the formulations is given in Table 4 hereinafter.

Initially, the formulations were produced by freezing the component compounds in liquid nitrogen with subsequent mixing in a grinding mill (A10 model, IKA Labortechnik, Neumagenstramβe, Germany) for a total of two minutes.

A more complete mixing of the components was found to be achieved by the use of a low volume stirrer. This apparatus consists of a stainless steel tube, closed at one end with a screw-in base and a router bit with a rubber seal connected to a variable speed drill. The compounds were placed into the tube and mated with the router bit. A 100% recovery of cream was achieved after mixing by unscrewing the base and inserting the plunger of a 10 ml syringe.

EXAMPLE 3

Diffusion Studies

Epidermal membranes consisting of predominantly stratum corneum with some attached keratinocytes was obtained from human skin taken during abdominal reduction operations and free of overt pathology. The skin was frozen and stored at −20° C. after excision until required. The epidermis was isolated by thawing the skin, removing the underlying fatty tissue and immersing in water at 60° C. for 45 seconds. The epidermal membranes could then be scraped away using a pair of forceps, floated on distilled water and mounted on aluminium foil dried in the air until excess water had evaporated then frozen and stored at −20° C. until required.

Assessment of topical skin protectants was carried out using Franz-type glass diffusion cells as previously described (Jenner et al., J. Pharm. Pharmacol. (1995) 47 206–212), with an area available for diffusion of 2.54 $cm^2$. Each diffusion cell consisted of an epidermal membrane placed on a metal gauze support forming a barrier between an upper (donor) and lower (receptor) chamber, both of which were initially filled with 0.9% saline.

The structural integrity of each membrane was determined by electrical resistance as previously described (Chilcott R. P. et al, Human and Experimental Toxicology, 14 (9) p773). Membranes with a resistance of less than 3.0 kΩ were judged to be damaged and were rejected from the study.

Following electrical resistance measurement, the receptor chamber fluid was replaced with 50:50 aqueous ethanol and the saline in the donor chamber was removed. Each formulation was applied as a 200 μl volume, giving a nominal thickness of 0.78 mm on the epidermal membrane surface. The protective compounds were also assessed individually without formulation by adding 200 mg directly to the donor chamber. Each formulation or compound was applied two hours before the addition of 20 μl [$^{35}$S]SM (50 μCi.ml$^{-1}$) as an airbourne droplet to the donor chamber. The experiments were subsequently conducted under occluded conditions in that the donor chamber was sealed with a plastic lid using contact adhesive (Bostik All Purpose Clear Adhesive).

Samples (20 μl) of receptor chamber fluid were taken at regular intervals for up to 60 hours. Each sample was replaced with an equivalent volume of 50:50 aqueous ethanol. The amount of radioactivity in each sample was measured by liquid scintillation counting in 5 ml Emulsifier Safe scintillation cocktail (Canbera Packard, Michigan USA), using a Rackbeta II 1215 scintillation counter. Amounts of radioactivity were related to amounts of SM determined from a sample of donor chamber liquid taken at the start of the study.

Figure 4:
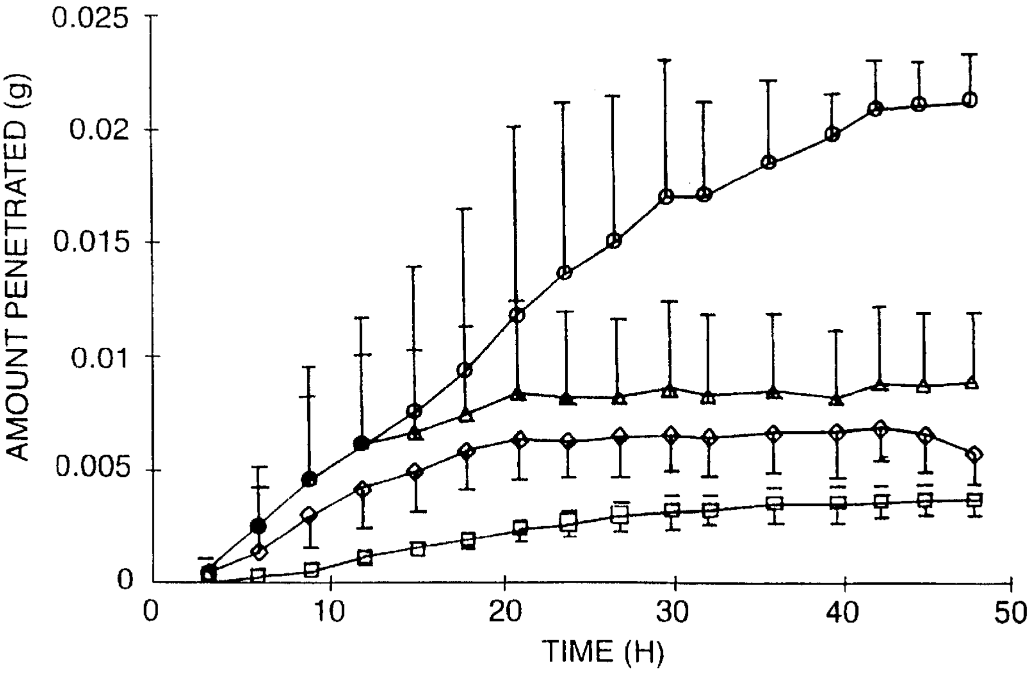
FIG. 4 is a graph showing penetration of $^{35}$S-radiolabelled sulphur mustard through human epidermal membranes. Points are mean±SD (n=4 to 6); where ℨ represents control, no barrier cream; Δ represents HMT alone, ♣ is HMT in Stokoderm base (20:80 w/w) and ◇ is HMT is Stokoderm base containing PTFE (20:50:30 w/w)
Figure 5:
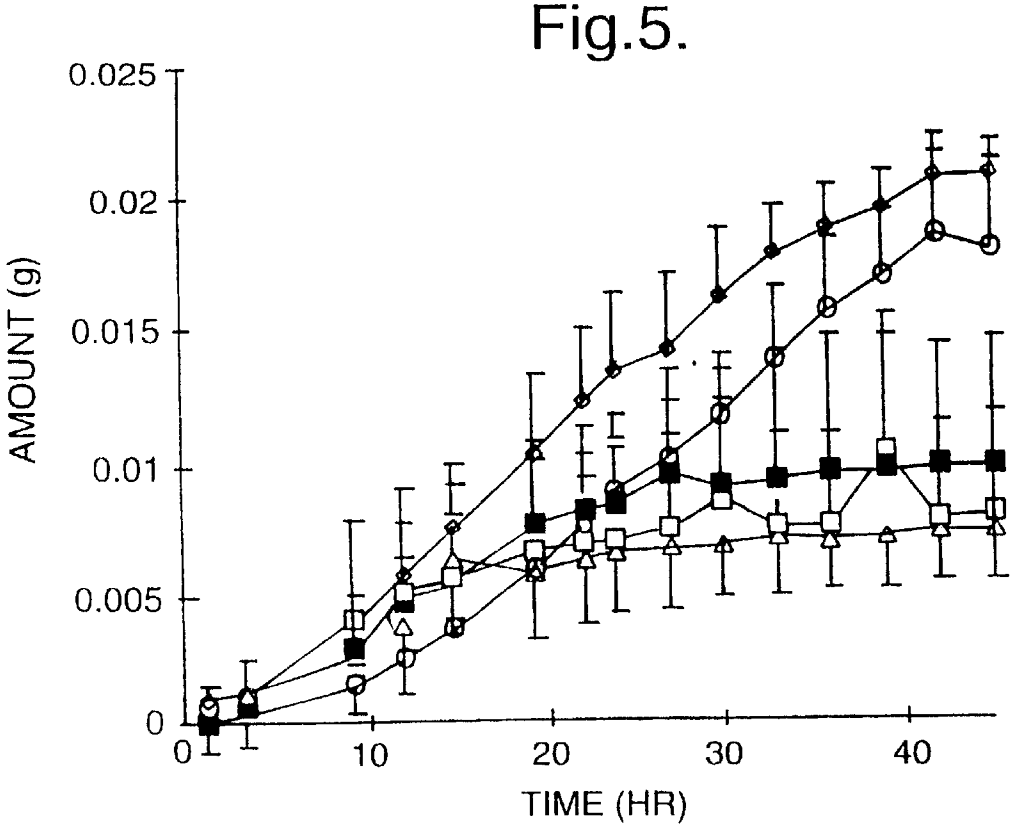
FIG. 5 is a graph showing penetration of $^{35}$S-radiolabelled sulphur mustard through human epidermal membranes. Points are mean±SD (n=4 to 6). HMT was mixed with each of the following cream bases at 30% (w/w) where ℨ represents control, no barrier cream; Δ represents 50% water, 5% beeswax, 15% Brij 52 and 30% heavy white mineral oil (% w/w), ♣ is 50% water 5% beeswax, 15% Brij 52 and polymethylhydrosiloxane (% w/w) and ■ is 50% water, 5% beeswax, 15% Brij 52 and 30% Dow Corning fluorinated oils (Fs300:Fs10000, 1:1) (% w/w); Polycysteine with a chain length of 5–15 kD was formulated into the following cream base at 30%-◇-50% water 5% beeswax, 15% Brij 52 and heavy white mineral oil (% w/w)

Results were analysed using a spreadsheet program (Excel, Microsoft Corp.) on a Mitac 486DX microcomputer. Results are presented as graphs of amount of radiolabelled SM penetrated with time and are shown in FIGS. 4 to 5. Where applicable, the maximum penetration rate achieved (Jmax), amounts penetrated at 6, 12 and 24 hours and total amount penetrated are summarised in Tables 2 and 3.

When used to prevent SM penetration through isolated epidermal membranes HMT, alone or formulated in Stokoderm cream reduced the total amount of SM which penetrated over 48 hours (FIG. 4).

HMT alone reduced the total penetrated to 42%±14% of non-pretreated controls, whereas when mixed with an oil in water cream base (Stokoderm) 17%±3% of controls penetrated. The addition of PTFE to the HMT:Stokoderm mixture allowed more SM to penetrate than HMT:Stokoderm, but not as much as HMT alone, 27%±10% of non-pretreated controls (Table 3).

TABLE 3

Summary of Percentage of Average Control Amount Penetrated Following Pretreatment With Topical Skin Protectants

| | % CONTROL AMOUNT PENETRATED | | | |
|---|---|---|---|---|
| PRETREATMENT | 6 h | 12 h | 24 h | 48 h |
| HMT | 116 ± 124 | 103 ± 64 | 60 ± 28 | 42 ± 14 |
| HMT in Stokoderm base (20:80, w/w) | 18 ± 5 | 19 ± 4 | 19 ± 4 | 17 ± 3 |
| HMT in stokoderm base with PTFE (20:50:30, w/w) | 61 ± 26 | 71 ± 30 | 46 ± 12 | 27 ± 10 |

% Control amount penetrated = the amount of SM penetrated through pretreated in comparison to control membranes expressed as a percentage at 6, 12 and 24 hours and at the termination of the experiment.

HMT alone had no effect on the maximum flux of SM penetration but mixing HMT with Stokoderm base or Stokoderm base containing PTFE resulted in maximum fluxes of 48±20 μg.cm$^{-2}$.hr$^{-1}$ and 178±86 μg.cm$^{-2}$.hr$^{-1}$ respectively (non-pretreated controls=233±181 μg.cm$^{-2}$.hr$^{-1}$) (Table 4).

TABLE 4

Quantitative Summary of SM Penetration Rates Following Pretreatment With Topical Skin Protectants

| TREATMENT | Jmax (μg · cm$^{-2}$ · hr$^{-1}$) |
|---|---|
| control (n) | 233 ± 181 |
| HMT in Stokoderm base (20:80, w/w)(n) | 48 ± 20 |
| HMT in stokoderm base with PTFE (20:50:30, w/w) (n) | 173 ± 86 |
| HMT (n) | 345 ± 278 |

Number in brackets indicates the number of epidermal membranes used in each study.

Formulation of HMT into an oil in water cream base consisting of water, beeswax, brij 52 and one of three oils (heavy white mineral oil, polymethylhydrosiloxane or fluorinated oils) also produced creams which reduced the total amount of SM penetrating over 48 hours but did not reduce the maximum flux rate (FIG. 5).

EXAMPLE 4

Diffusion Studies Using Perfluorinated Polymer Barrier Creams

Assessment of topical skin protectants was carried out using Franz-type glass diffusion cells substantially as previously described (Jenner et al., J. Pharm. Pharmacol. (1995) 47 206–212), with an area available for diffusion of 2.54 $cm^2$. In this case however, each diffusion cell consisted of a rubber latex membrane (26% ethylene vinyl acetate (EVA), RMCS Shrivenham) placed on a metal gauze support forming a barrier between an upper (donor) and lower (receptor) chamber.

Previous studies had shown that this apparatus, including the rubber latex membrane would provide a suitable model for identifing compounds with a barrier function and that penetration rates provide a quantitative method of assessing the retardant properties of the compounds.

The receptor chamber fluid was filled with 50:50 aqueous ethanol. Each composition was applied as a 200 μl volume, giving a nominal thickness of 0.8 mm on the membrane surface. Each composition was applied two hours before the addition of 20 $\mu$l [$^{35}$S]SM (50 $\mu$Ci.ml$^{-1}$) as an airborne droplet to the donor chamber. The experiments were subsequently conducted under occluded conditions in that the donor chamber was sealed with a plastic lid using contact adhesive (Bostik All Purpose Clear Adhesive).

Samples (20 $\mu$l) of receptor chamber fluid were taken at regular intervals for up to 8 hours. Each sample was replaced with an equivalent volume of 50:50 aqueous ethanol. The amount of radioactivity in each sample was measured by liquid scintillation counting in 5 ml Emulsifier Safe scintillation cocktail (Canbera Packard, Michigan USA), using a Rackbeta II 1215 scintillation counter. Amounts of radioactivity were related to amounts of SM determined from a sample of donor chamber liquid taken at the start of the study.

Figure 6:
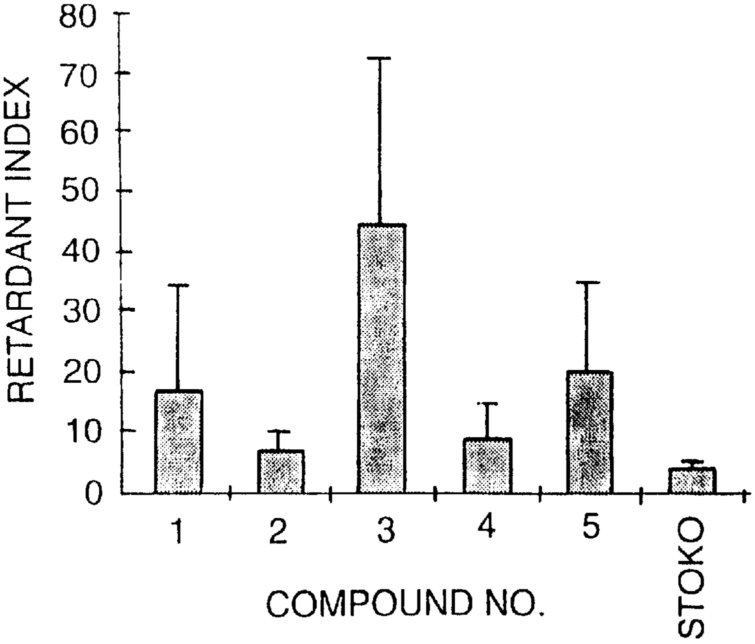
FIG. 6 is a graph showing the ability of perfluorinated polymers to retard the rate of penetration of SM (expressed as retardation index). "Stoko" is an abbreviation for the commercially available barrier cream Stokoderm® consisting of an oil-in-water emulsion and was included for comparison (positive control)
Figure 7:
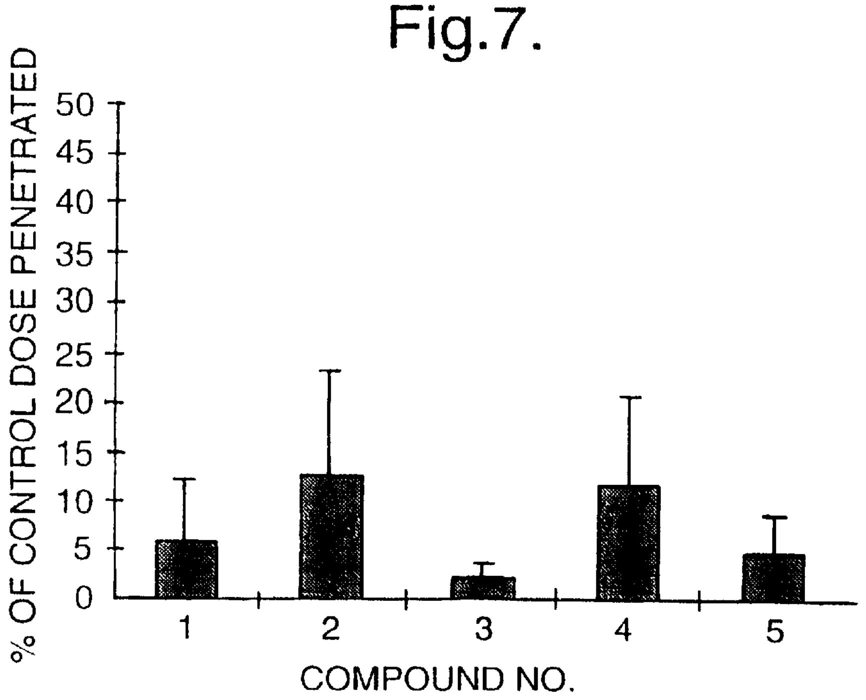
FIG. 7 is a graph showing the amount of SM penetrated through pretreated membranes expressed as percentage of control amount penetrated after 3 hours.

Results were initially plotted as total amount of $^{35}$S-radiolabelled sulphur mustard penetrated against time. During the first four hours, a straight line is observed (the maximum penetration rate, $J_{max}$). From this, the retardant index could be calculated and the results are shown in FIG. 6

Figure 2:
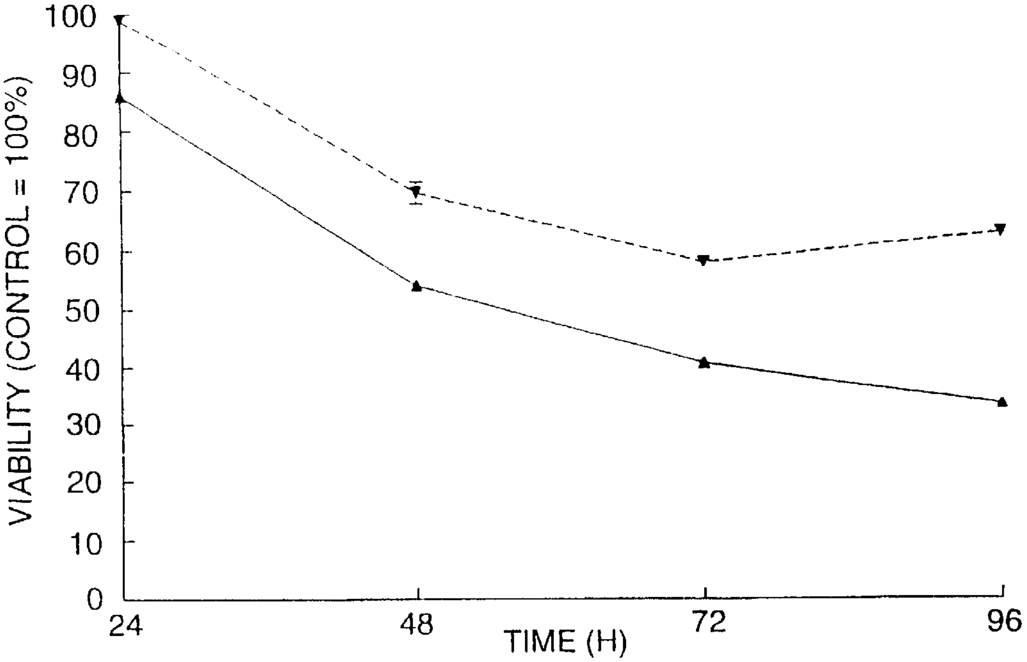
FIG. 2 shows the effect on viability of pretreatment of SVK-14 cultures with a mixture of 4 mM GSH/10 mM HMT prior to exposure to 10 μM SM. Viability of pretreated cultures (▼) and those only exposed to SM (▲) was measured by the NR assay. Data are shown as the mean±S.E.M. (n=15) expressed as a percentage of the untreated control.

In addition, the total amount of SM penetrated through the membranes over three hours was calculated and expressed as a percentage of the untreated control. The results are shown in FIG. 2.

It can be seen from these Figures that the compositions of the invention provide significant protective barrier effects and are more effective than a commercially available barrier cream.

EXAMPLE 5

Figure 8:
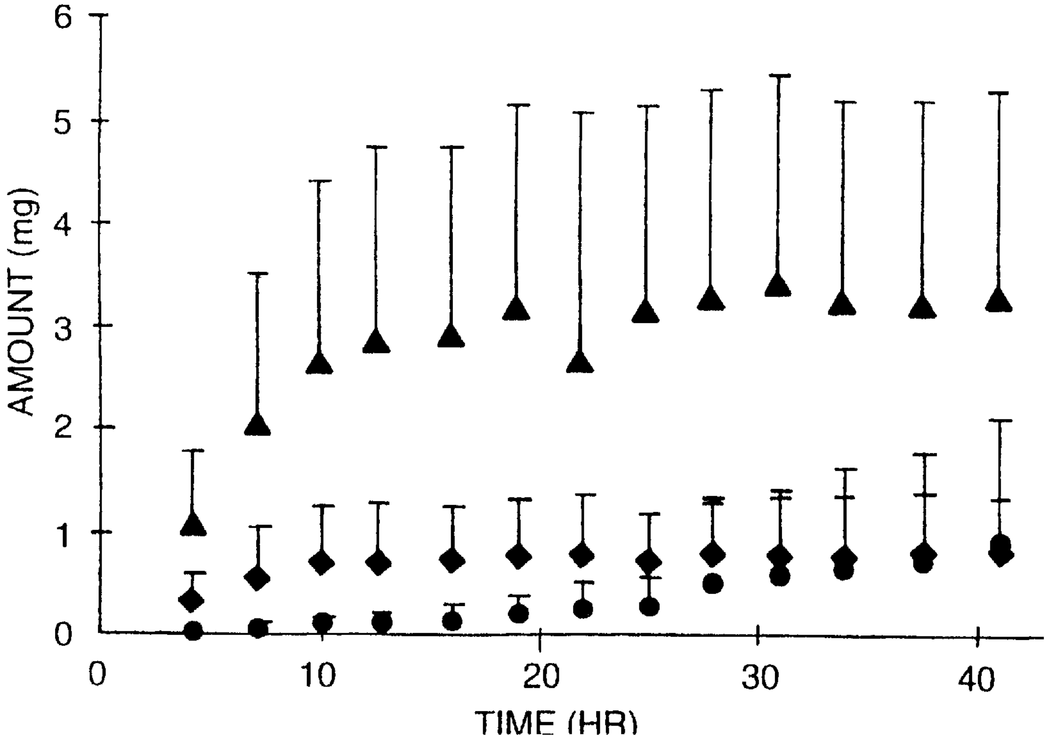
FIG. 8 is a graph showing SM penetration through human skin under unoccluded conditions pretreated with Fomblin-Z-diol™ (●), a comercially available barrier cream (Stokoderm™) with a reactive thiol ester (▲) and an untreated control (♦)
Figure 9:
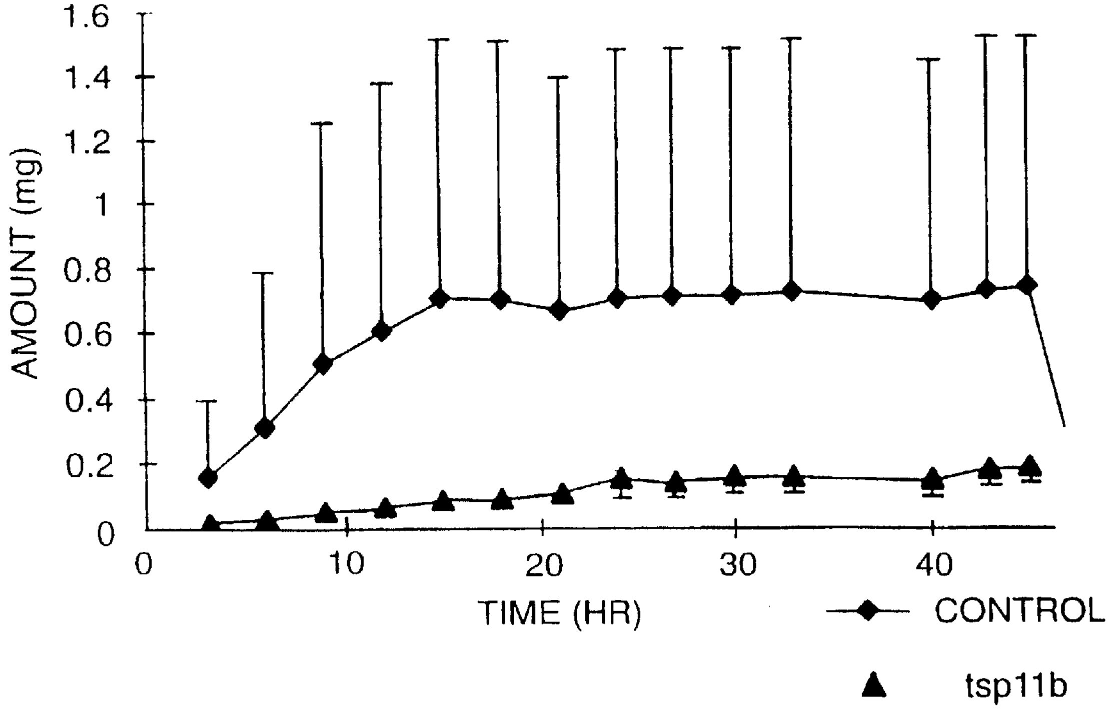
FIG. 9 is a graph showing SM penetration under unoccluded conditions through skin pretreated with a formulation in accordance with the invention (▲) and an untreated control (♦)

Comparison of SM Penetration Through Skin Pretreated With Perfluorinated Polymer Barrier Oil and Commercially Available Barrier Cream Using methodology substantially as described in Example 3 above, the effect of pretreating the skin samples with Fomblin-z-diol™ two hours before addition of liquid SM is shown in FIG. 8. The experiment was effected under unoccluded conditions (where the SM is free to vaporise off the skin surface), and a standard barrier cream (an oil-in-water emulsion) containing a reactive thiol compound and an untreated control was used for comparison purposes.

It was found that under these conditions, the oil-in-water cream increased the total amount of mustard penetrated. In practical terms, a user "protected" with this cream would receive a higher dose and possibly a more severe mustard skin injury than unprotected bare skin. In contrast, the Fomblin provided protection for up to 35 hours. This protection is significant for the first 12 hours. Furthermore, the droplet of mustard on the Fomblin treated skin surface can be easily moved, indicating that on a vertical surface, very little or no mustard would penetrate. The maximum protective effect of Fomblin-z-diol (measured as the percentage decrease in total mustard penetrated) was calculated as 92% at 3 hours, 84% at 12 hours and 61% at 24 hours.

EXAMPLE 6

Effect of Mixture of Fomblin and PTFE

A formulation was produced by mixing 76% Fomblin HC/R™ and 24% PTFE (polytetrafluoroethylene) at 1800 rpm at room temperature for 4 hours. Example 5 was then repeated using this formulation and an untreated control. The results are shown in FIG. 8.

It is clear that the inclusion of PTFE has had a profound effect in that the pretreated skin has approximately 75% less mustard penetrated than controls, and this decrease is present for the whole experiment (over 45 hours). The maximum protective effect of this formulation (measured as the percentage decrease in total SM penetrated) was 90% at 3 hours, 90% at 12 hours, 75% at 24 hours and 75% at the end of the experiment.

This was found to be better than the use of Fomblin HC/R alone which is indicative of the beneficial effects of PTFE.

EXAMPLE 7

Formulation of Active Barrier Creams

The following formulations were prepared:

Formulation A:

93% Fomblin™ HC/R 6.6% aqueous saturated HMT solution 0.4% Brij 30

0.4% cetyl alcohol

A small volume of Fomblin ™ HC/R was mixed with the Brij 30 and cetyl alcohol at 50° C. and the mixture added to the rest of the Fomblin ™ HC/R and saturated HMT solution at room temperature with constant mixing using a Hiedolf constant torque stirrer at 1800 rpm.

Formulation B 0.08% Brij 52

1.16% aqueous saturated HMT 98.76% Fomblin™ HC/R

In this case, Fomblin ™ HC/R was heated to 40° C. and the Brij 52 and HMT solutions were added. The mixture was heated to 70° C. with constant stirring (1800 rpm) and allowed to cool to room temperature also with constant stirring.

Figure 10:
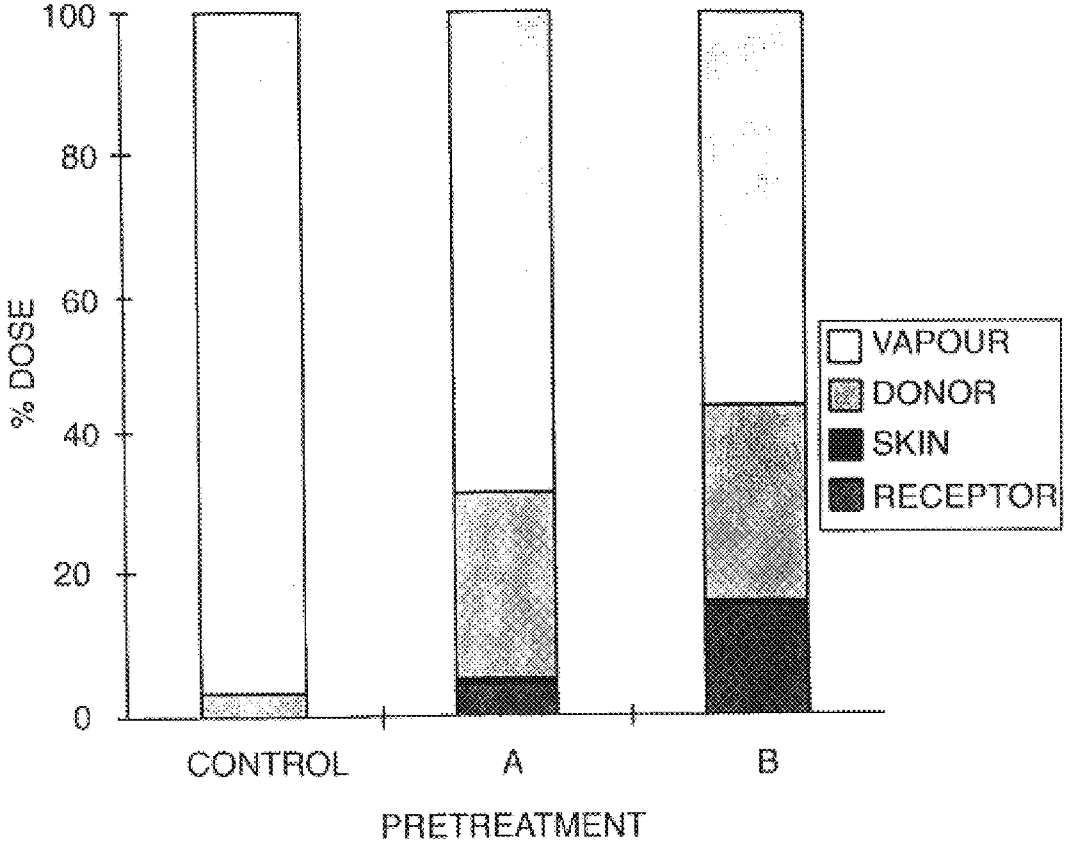
FIG. 10 shows the percentage radiolabelled SM distribution in a receptor chamber (penetrated SM), skin, donor chamber (reacted SM) and vapour.

The formulations were subjected to diffusion studies as described above in Example 3 under unoccluded conditions. The reactivity of the barrier creams was qualitatively measured by measuring the amount of radioactivity remaining in the donor chamber as compared to the receptor, the vapour and the skin at the end of the experiment, when no more penetration of radiolabelled SM was occuring. The results are shown in FIG. 10.

The control (un-pretreated) skin had little or no mustard on the surface (donor chamber) whereas both reactive barrier cream formulations contained radioactivity, implyin that the radiolabelled mustard had reacted with the HMT to form a stable, non-penetrating adduct. This was further substantiated be the fact that similar formulations without HMT had residual donor chamber radioactivity equal to that of the control.

EXAMPLE 8

Preparation of N-octadecyl Hexaminium Halide Salts 1-bromo octadecance (12.0 g) was added to sodium iodide (5.5 g) in methyl iso butyl ketone and the stirred suspension refluxed for 3 hours. The suspension acquired an opalescent appearence after 25 minutes. Estimation of conversion was made by determining unreacted iodide with copper sulphate. A conversion of approximately 90% was achieved and this material was used without further purification.

1-iodo octadecane (crude, 13.3 g) was refluxed with hexamethylene tetramine in chloroform (40 ml) as previously. The suspension cleared briefly and then a precipitate formed. After cooling and stirring for 40 hours, the white solid was filtered and washed with chloroform (2×7 ml) and then cyclohexane (7 ml) and then dried in vacuo at 30–40° C. Yield: 3.9 g.

The ionic iodide was determined argenotmetrically: 24.03%; (theoretical 24.37%), i.e. 98.6% of the expected figure. Melting point: 146–150° C. with decomposition. The structure was confirmed by IR.

This product may be converted to the bromide salt using a suitable ion exchange column.

EXAMPLE 9

Preparation of 2 Pentafluorobenzyl Hexaminium Bromide

In dry glassware, α-bromo-2,3,4,5,6-pentafluorotoluene (5.02 g) and hexamethyiene tetramine (3.0 g) were refluxed in chloroform (20 ml). The headspace was purged in nitrogen and a drying tube was used to maintain anhydrous conditions. The suspension was warmed to effect solution. A precipitate formed after a few minuted and thickened over 40 minutes. A temperature rise of 3 degrees above ambient was experienced. After stirring for 2.5 hours at ambient temperature, the suspension was taken to reflux and allowed to cool. The thick paste was filtered and washed with chloroform (3×5 ml). The resulting solid was dried in vacuo at 30–40° C. Yield:6.84 g. m.p. 206–208° C., decomposition. Water solubility: 1 g dissolves in 11 ml at 20° C. (equivalent to 90 $mg.ml^{-1}$).

The ionic bromide was determined using an excess of silver nitrate solution followed by back-titration with potassium thiocyanate to give an assay of 99.3%. The structure of the compound was confirmed by I.R.

EXAMPLE 10

Reactivity of HMT Analogues

The reactivity of the analogues of HMT produced in Examples of 8 and 9 above was tested as follows. The following solutions were prepared:

a. HMT (140.19 mg) in THF (10 ml).

b. N-octadecyl HMT (406.70 mg) in THF (10 ml)

c. Pefluorobenzyl HMT (387.46 mg) in tetrahydrofimran (THF) (10 ml);

To each solution, radiolabelled sulphur mustard (124.9 μl) ($^{35}S$) was added. After one hour, 20 μl samples were removed and placed onto a silica TLC plate in lanes 2–4 respectively with a drop of $^{35}S$-SM (lane 1) and were chromatographed with a THF mobile phase for approximately 40 minutes. The TLC plate was then removed and autoradiographed using Kodak Biomax x-ray film.

Figure 11:
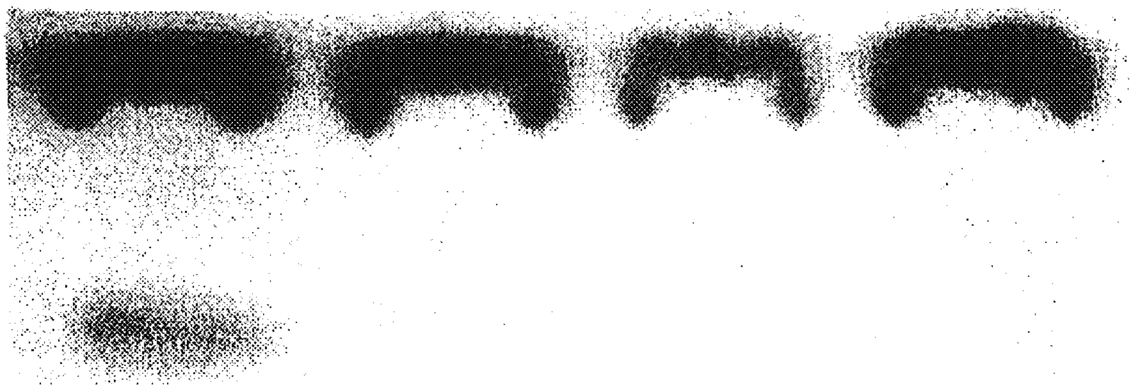
FIG. 11 shows an autoradiograph of a TLC plate from samples of HMT and analogues which had been allowed to react with radiolabelled SM.

The TLC results are shown in FIG. 11. It is noticeable that free H is only present in the contol sample. No free H is present in solutions containing reactive compounds HMT and the octadecyl and perfluorobenzyl analogue thereof.

What is claimed is:

1. A barrier cream composition comprising 90–99% w/w of a perfluorinated compound of formula (IV)

$$CF_3O\text{-}[CF(CF_3)CF_2O]_n[CF_2O]_m\text{ -}CF_3 \quad (IV)$$

where n and m are independently selected from 4 to 150, further comprising a lower molecular weight perfluorinated compound and further comprising an amount of hexamethylene tetramine or analogue or derivative equivalent to that contained with 0.5–10% w/w of a saturated aqueous solution of hexamethylene tetramine, saturation being determined at room temperature.

2. A barrier cream composition comprising 30 to 100% w/w of a perfluorinated polymeric compound of formula (IV)

$$CF_3O\text{-}[CF(CF_3)CF_2O]_n[CF_2O]_m\text{-}CF_3 \quad (IV)$$

where n and m are independently selected from 4 to 150, further comprising a lower molecular weight perfluorinated compound and further comprising an hexamethylene tetramine derivative of formula (II)

(II)

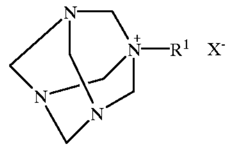

where $R^1$ is an organic group and $X^-$ is a anion.

3. A barrier cream composition according to claim 1 or 2 wherein the lower molecular weight perfluorinated compound is polytetrafluoroethylene (PTFE).

4. A barrier cream composition according to claim 2, wherein $R^1$ is an optionally substituted, straight or branched hydrocarbon chain having from 1 to 50 carbons atoms.

5. A barrier cream composition according to claim 2, wherein $R^1$ is an optionally substituted, straight or branched hydrocarbon chain having from 1 to 50 carbon atoms and wherein the hydrocarbon chains are optionally substituted by one or more substitutents selected from aryl optionally substituted by halogen, and halogen.

6. A barrier cream composition according to claim 2, wherein $R^1$ is an optionally substituted straight or branched hydrocarbon chain having from 1 to 50 carbon atoms and wherein the hydrocarbon chains are optionally substituted by one or more substituents selected from aryl optionally substituted by halogen, and halogen, and wherein $R^1$ is a fluorobenzyl or a group $(CH_2)_nCH_3$ where n is from 8 to 20.

7. A process for protecting the skin of a human or animal against volatile chemical agents which consists of applying to the skin a barrier cream composition according to claim 1 or 2.

* * * * *